United States Patent [19]
Sonobe et al.

[11] Patent Number: 4,765,988

[45] Date of Patent: Aug. 23, 1988

[54] AMOSULALOL HYDROCHLORIDE LONG ACTING FORMULATIONS

[75] Inventors: Takashi Sonobe; Hiroshi Sugiura, both of Saitama; Tomoh Itoh, Tokyo; Masayoshi Aruga; Hiroitsu Kawata, both of Saitama, all of Japan

[73] Assignee: Yamanouchi Pharmaceutical Co., Ltd., Tokyo, Japan

[21] Appl. No.: 46,266

[22] Filed: May 5, 1987

Related U.S. Application Data

[60] Division of Ser. No. 931,924, Nov. 14, 1986, Pat. No. 4,724,148, which is a continuation of Ser. No. 645,618, Aug. 29, 1984, abandoned.

[30] Foreign Application Priority Data

Aug. 31, 1983 [JP]  Japan ................................ 58-160086

[51] Int. Cl.$^4$ .......................... A61K 9/32; A61K 9/36; A61K 9/34
[52] U.S. Cl. .................................. 424/468; 424/474; 424/480; 424/482
[58] Field of Search ................ 424/468, 474, 480, 482

[56] References Cited

U.S. PATENT DOCUMENTS

| | | | |
|---|---|---|---|
| 3,520,970 | 7/1970 | Lehmann et al. | 424/25 |
| 3,538,214 | 11/1970 | Polli et al. | 424/19 |
| 3,775,537 | 11/1973 | Lehmann et al. | 424/21 |
| 3,835,221 | 9/1974 | Fulberth et al. | 424/20 |
| 3,954,959 | 5/1976 | Pedersen | 424/20 |
| 4,083,949 | 4/1978 | Benedikt | 424/19 |
| 4,289,750 | 9/1981 | Kopp et al. | 424/33 |
| 4,361,546 | 11/1982 | Stricker et al. | 424/19 |
| 4,367,217 | 1/1983 | Gruber et al. | 424/19 |
| 4,427,648 | 1/1984 | Brickl et al. | 424/21 |
| 4,438,091 | 3/1984 | Gruber et al. | 424/21 |
| 4,724,148 | 2/1988 | Sonobe et al. | 424/480 |

*Primary Examiner*—Shep K. Rose
*Attorney, Agent, or Firm*—Burgess, Ryan & Wayne

[57] ABSTRACT

Long acting formulations of amosulalol hydrochloride are provided, wherein the frequency of administering the hypotensive agent is minimized and wherein such formulations are prepared by compounding amosulalol hydrochloride with an enterosoluble material and optionally the inclusion of an organic acid.

5 Claims, 3 Drawing Sheets

AMOSULALOL HYDROCHLORIDE LONG ACTING FORMULATIONS

This is a division of application Ser. No. 931,924, filed Nov. 14, 1986, now U.S. Pat. No. 4,724,148 which is a continuation of Ser. No. 645,618, filed Aug. 29, 1984, now abandoned.

FIELD OF THE INVENTION

This invention relates to a long acting formulation of amosulalol hydrochloride (chemical name: 5-{1-hydroxy-2-[2-(2-methoxyphenoxy)ethylamino]ethyl}-2-methylbenzenesulfonamide hydrochloride).

BACKGROUND OF THE INVENTION

Amosulalol hydrochloride is an excellent hypotensive agent having an adrenergic α-blocking action and an adrenergic β-blocking action. In general, it is desirable that the frequency of administering a hypotensive agent be minimized from the simplicity of clinical therapy but considering the biological half life of amosulalol hydrochloride, it is difficult to realize the above-described goal by conventional formulations.

SUMMARY OF THE INVENTION

As the result of various investigations, the inventors have discovered that a formulation prepared by compounding amosulalol hydrochloride with the usual excipients and adding thereto an entero-soluble material has excellent long acting characteristics and further by adding a pharmaceutically acceptable organic acid to the formulation, the solubilization of amosulalol hydrochloride in a high pH range is promoted and the bioavailability thereof can be increased.

Thus, according to this invention, there is provided an amosulalol hydrochloride long acting formulation comprising amosulalol hydrochloride and an entero-soluble material.

According to another embodiment of this invention, there is further provided an amosulalol hydrochloride long acting formulation comprising amosulalol hydrochloride, an entero-soluble material and a pharmaceutically acceptable organic acid.

By the formulation of this invention, it becomes possible to maintain the minimum effective plasma level of amosulalol hydrochloride for a long period of time without increasing the plasma level beyond what is necessary.

DESCRIPTION OF THE PREFERRED EMBODIMENT

Figure 1:
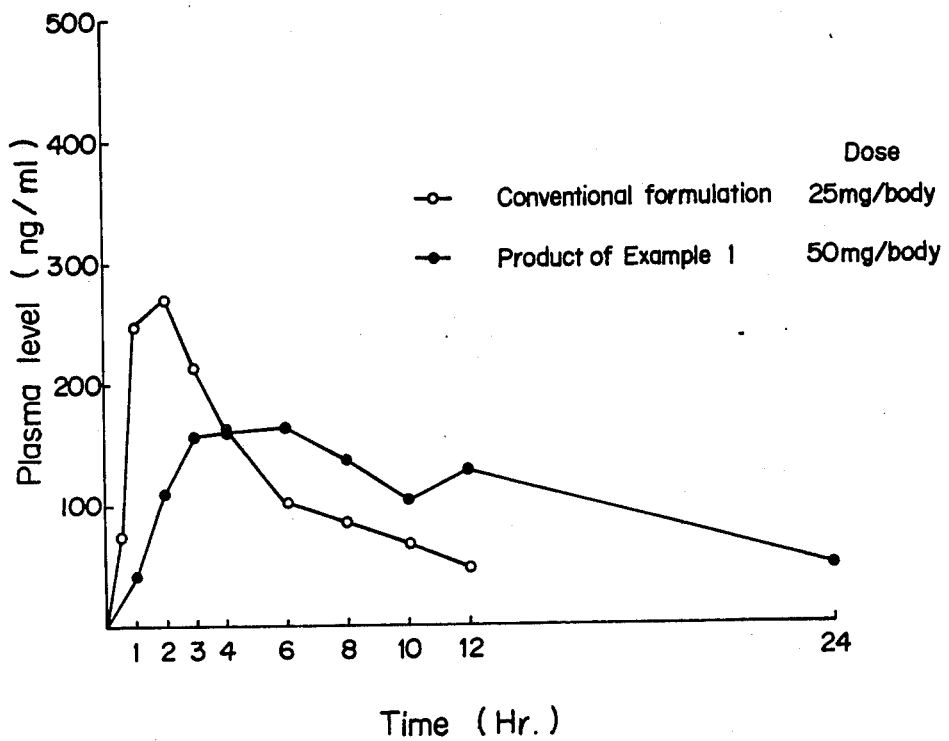
FIG. 1 shows plasma level of amosulalol hydrochloride in a single-blind cross-over study as a function of time following oral administration of the long acting formulation of this invention prepared in Example 1 or a conventional formulation of amosulalol hydrochloride.

The formulation of this invention can be prepared by the following manner.

Amosulalol hydrochloride is mixed well with an excipient which may be selected from those usually used and after adding thereto a solution or a suspension of an entero-soluble material in water or an organic solvent, the resultant mixture is granulated. In this case, the entero-soluble material may be directly added to the aforesaid mixture of amosulalol and after adding thereto a binder which may be selected from those usually used, the resultant mixture may be granulated. Also, in the case of using a pharmaceutically acceptable organic acid in this invention, the organic acid may be added to the aforesaid mixture followed by granulation. Furthermore, the granules thus obtained may be formed into tablets by means of a tableting machine and coating may be applied to these tablets for the prevention of bitterness and the improvement of the appearance.

Examples of the entero-soluble material which is used in this invention are a methacrylic acid-ethyl acrylate copolymer (e.g., Eudragit L30D-55, trade name made by Rohm and Haas Company, a copolymer of methacrylic acid and ethyl acrylate (1:1) having a molecular weight of about 250,000), a methacrylic acid-methyl methacrylate copolymer (e.g., Eudragit L100, trade name, made by Rohm and Haas Company, a copolymer of methacrylic acid and methyl methacrylate (1:1) having a molecular weight of 135,000 or Eudragit S100, a copolymer of methacrylic acid and methyl methacrylate (1:2) having a molecular weight of about 135,000), hydroxypropylmethyl cellulose phthalate (The Japan Pharmacopoeia, the 10th Revision), cellulose acetate phthalate (The Japan Pharmacopoeia, the 10th Revision), shellac (The Japan Pharmacopoeia, the 10th Revision), and the like.

These entero-soluble materials are dissolved at a pH higher than a specific value. For example, Eudragit L30D-55 is dissolved at a pH higher than about 5.5, Eudragit L100 at a pH higher than about 6.0, and Eudragit S100 at a pH higher than about 7.0.

By properly selecting the entero-soluble material, the medicament can be absorbed at each different portion in the intestines, thus the long acting characteristics can be controlled. Among the above-described entero-soluble materials, methacrylic acid-ethyl acrylate copolymers can be dissolved in water as a solvent and hence in this case the granulation is easy as compared to the case of using an organic solvent and also this case is safe and economical. In addition, a methacyrlic acid-ethyl acrylate copolymer (Eudragit L30D-55) is commercially available in the form of usually an aqueous 30% dispersion.

The entero-soluble material is used in a content of 5 to 50% by weight of the total weight of the formulation of this invention and the content of 10 to 30% by weight is particularly preferred.

Examples of the pharmaceutically acceptable organic acids which are used in this invention are citric acid (The Japan Pharmacopoeia, the 10th Revision), tartaric acid (The Japan Pharmacopoeia, the 10th Revision), and the like. The purpose of using the organic acid is to improve the solubility of amosulalol hydrochloride at a high pH region (in particular, about 7.5 which is one of the pH values of a physiological saline solution), whereby the bio-availability of amosulalol hydrochloride is increased. The content of the pharmaceutically acceptable organic acid is 1 to 30% by weight of the total weight of the product but is, in particular, preferably 5 to 20% by weight.

In this invention, excipients, lubricants, binders, and the like, which are usually used for conventional formulations can be used without particular restrictions. Examples of the excipients are lactose, starch, calcium hydrogenphosphate, silicic anhydride, and the like. Examples of the lubricants are magnesium stearate, talc, and the like; and examples of the binders are hydroxypropyl cellulose, starch, and the like. There is no particular restriction on the amounts of these additives and the amounts of them may be properly selected according to the purpose of using them.

Then, the present invention will be further explained by the following examples but is not limited thereby in any way.

EXAMPLE 1

In a fluidized bed/granulator were placed 500 g of amosulalol hydrochloride and 500 g of lactose and the products sufficiently mixed. To the mixture was sprayed an aqueous dispersion of a methacrylic acid-ethyl acrylate copolymer (Eudragit L30D-55) in an amount of 240 g as a solid component and granules were formed from the mixture by mean of a fluidized bed granulator. After drying the granules thus obtained for 4 hours at 40° C., 6 g of magnesium stearate was added to the granules and the mixture was formed into tablets by means of an ordinary tableting machine.

Each of the formulation of this invention (containing 50 mg of amosulalol hydrochloride) and a conventional formulation (containing 25 mg of amosulalol) containing no entero-soluble material was orally administrated to each healthy adult man once a day by a crossover method with wash-out period of one week. In the case of using the tablets of this invention, the amosulalol hydrochloride concentration in the plasma was measured by a high pressure liquid chromatographic analysis after 1, 2, 3, 4, 6, 8, 10, 12 and 24 hours since the administration, while in the case of using the conventional tablets, the amosulalol hydrochloride concentration in the plasma was measured by the same manner as above after 1, 2, 3, 4, 6, 8, 10 and 12 hours since the administration. The results are shown in FIG. 1.

As shown in the figure, it can be seen that by the administration of the formulation of this invention once a day, the concentration of amosulalol hydrochloride in the plasma can be sufficiently prolonged as compared to the case of using the conventional formulation.

EXAMPLE 2

In a fluidized bed dryer were mixed 200 g of amosulalol hydrochloride, 50 g of silicic anhydride and 30 g of hydroxypropyl cellulose and after spraying thereto a solution prepared by dissolving 20 g of citric acid in an aqueous dispersion of a methacrylic acid-ethyl acrylate copolymer (Eudragit L30D-55), granules were produced from the mixture using a fluidized bed granulator. To the granules thus formed was added 1.6 g of magnesium stearate and the mixture was formed into tablets by means of an ordinary tableting machine.

By the method as performed on the product in Example 1, the amosulalol hydrochloride concentration in the plasma was compared between the case of using the formulation of this invention and the case of using the conventional formulation using beagle dogs. The results are shown in FIG. 2.

Figure 2:
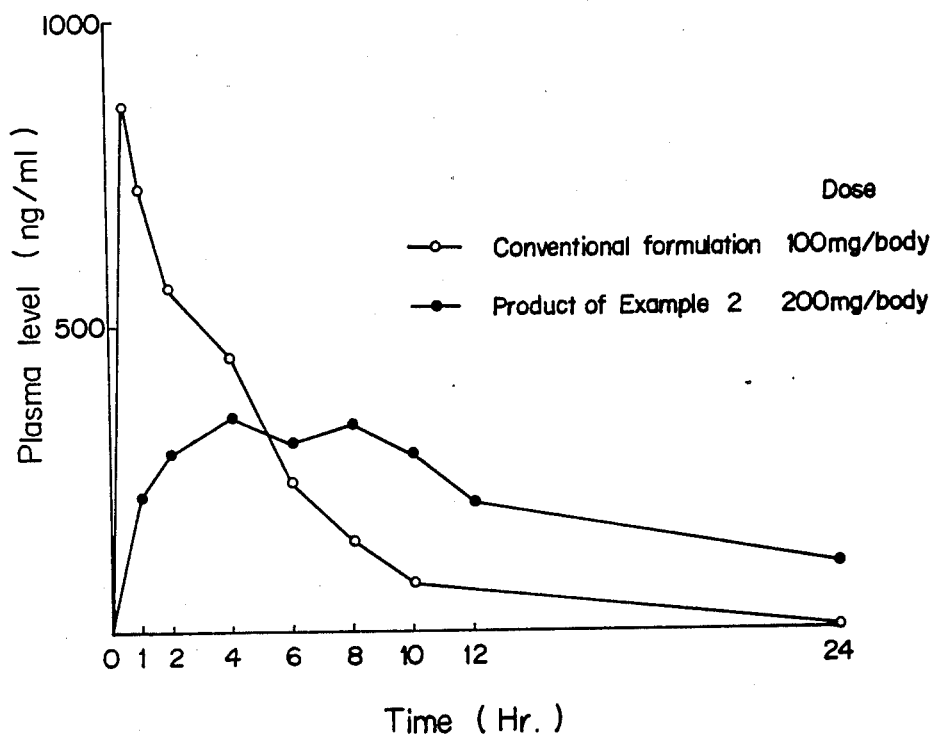
FIG. 2 shows plasma level of amosulalol hydrochloride in a single-blind cross-over study as a function of time following oral administration of the long acting formulation of this invention prepared in Example 2 and a conventional formulation of amosulalol hydrochloride. The data represents the mean of five determinations in beagle dogs.

As shown in FIG. 2, it can be seen that in the case of using the formulation of this invention, the concentration of amosulalol hydrochloride in the plasma can be sufficiently prolonged as compared to the case of using the conventional formulation.

EXAMPLE 3

In a vertical mixer were mixed 200 g of amosulalol hydrochloride, 30 g of citric acid and 60 g hdyroxypropylmethyl cellulose phthalate (HP-55, trade name) and after adding gradually thereto 64 g of an aqueous solution of 10% hydroxypropyl cellulose under stirring, granules were formed from the mixture. After drying granules thus formed for 4 hours at 40° C., 1.6 g of magnesium stearate was added to the granules and the resultant mixture was formed into tablets by means of a tableting machine.

By the method as performed on the product in Example 1, the amosulalol hydrochloride concentration in the plasma was compared between the case of using the formulation of this invention and the case of using an aqueous 1% amosulalol hydrochloride in beagle dogs. The results are shown in FIG. 3.

Figure 3:
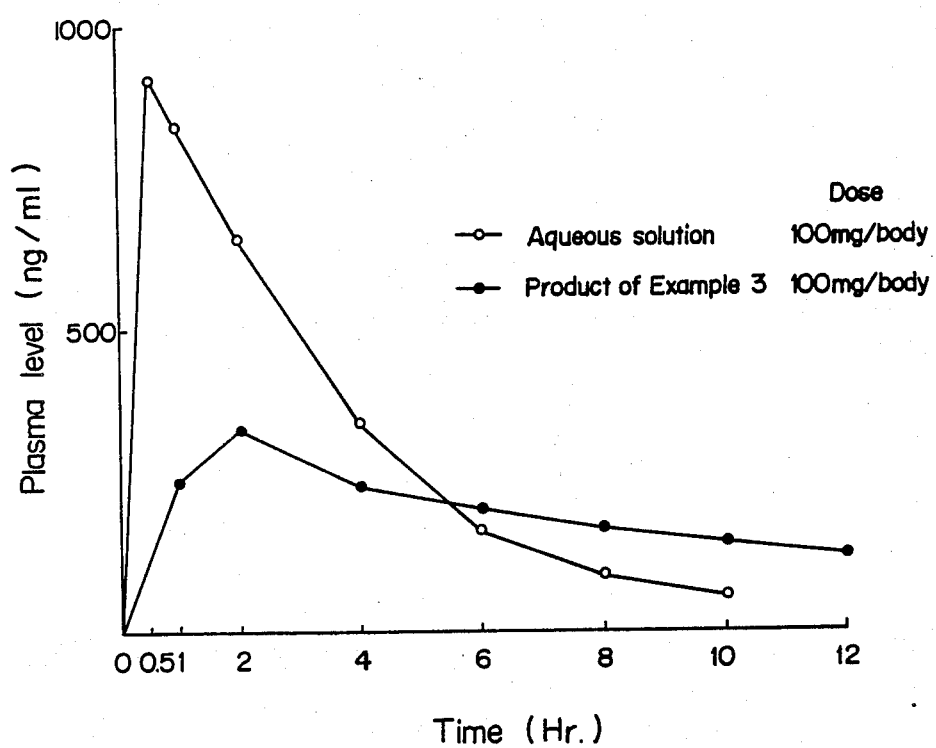
FIG. 3 shows plasma level of amosulalol hydrochloride in a single-blind cross-over study as a function of time following oral administration of the long acting formulation of this invention prepared in Example 3 and an aqueous solution of amosulalol hydrochloride. The data represents the mean of six determinations in beagle dogs.

As shown in FIG. 3, it can be seen that in the case of using the formulation of this invention, the concentration of amosulalol in the plasma can be sufficiently prolonged as compared to the case of using the aqueous solution of amosulalol.

What is claimed is:

1. A long acting pharmaceutical formulation comprising pharmaceutically effective amounts of amosulalol hydrochloride, from about 5 to about 50 weight percent of said formulation of an entero-soluble material selected from the group consisting of a methacrylic acid-ethyl acrylate copolymer, a methacrylic acid-methyl methacrylic copolymer, hydroxypropylmethyl cellulose phthalate, cellulose acetate phthalate and shellac, and the balance being at least one pharmaceutically acceptable additive excluding any pharmaceutically acceptable organic acid.

2. A formulation of claim 1 wherein the entero-soluble material is a methacrylic acid-ethyl acrylate copolymer.

3. A method for the treatment of a subject afflicted with hypertension which comprises administering to said subject an antihypertensive effective amount of the long acting formulation of claim 1.

4. The method of claim 3 wherein the entero-soluble material is a methacrylic acid-ethyl acrylate copolymer.

5. The method of claim 3 wherein the entero-soluble material is a methacrylate acid-methylmethacrylate copolymer.

* * * * *